US00PP37822P2

(12) United States Plant Patent
Mathey

(10) Patent No.: US PP37,822 P2
(45) Date of Patent: Oct. 27, 2026

(54) ***BUDDLEIA* PLANT NAMED 'SMNBDFRI'**

(50) Latin Name: *Buddleia davidii*
Varietal Denomination: SMNBDFRI

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,904

(22) Filed: Oct. 28, 2025

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ..... A01H 5/02; A01H 5/00; A01H 6/00
See application file for complete search history.

(56) References Cited

U.S. PATENT DOCUMENTS

PP34,515 P3 * 8/2022 Koot ..... Plt./242

* cited by examiner

*Primary Examiner* — June Hwu

(57) ABSTRACT

A new and distinct cultivar of *Buddleia* plant named 'SMNBDFRI' is disclosed, characterized by large, conical inflorescences of bright, magenta-colored petals with a floral fragrance. Plants are dwarf and compact with large, dark green leathery foliage. The new cultivar is a *Buddleia,* typically produced as an outdoor ornamental plant.

2 Drawing Sheets

Figure 1:
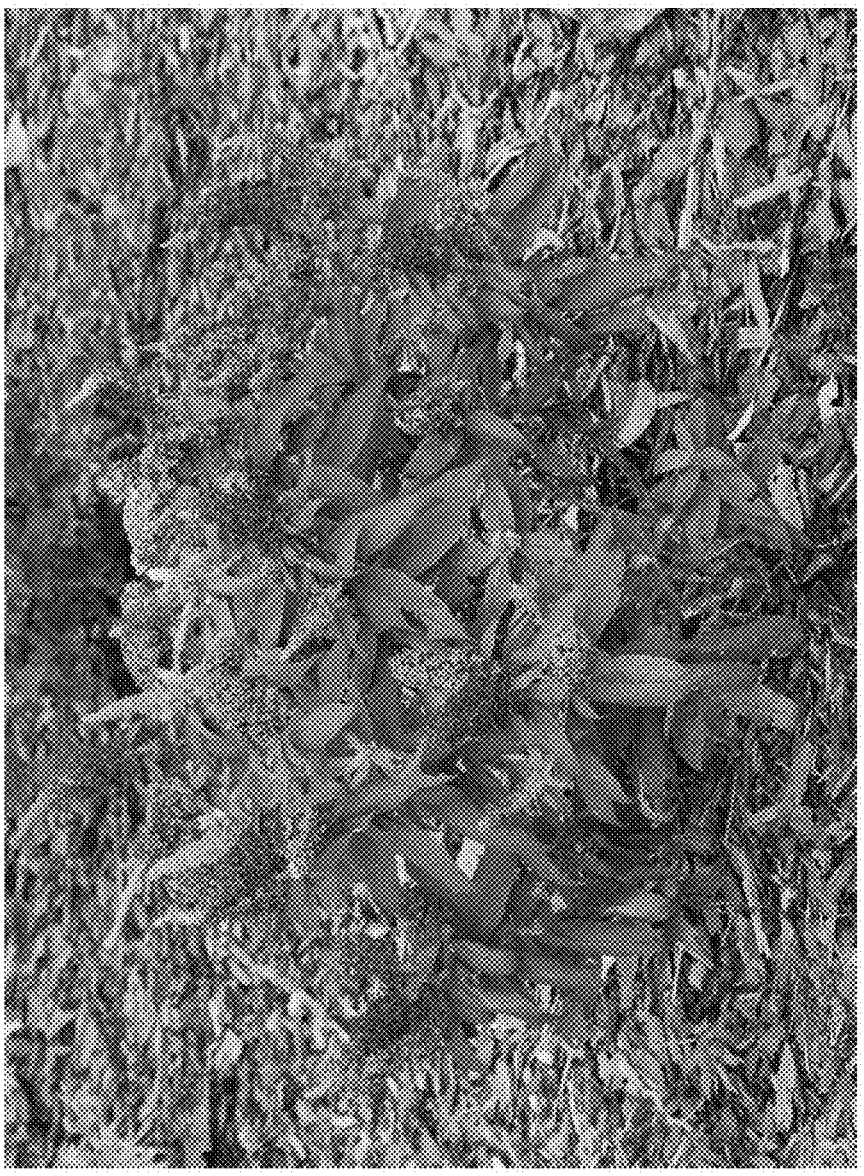

Latin name of the genus and species: *Buddleia davidii.*
Cultivar denomination: 'SMNBDFRI'.

BACKGROUND OF THE INVENTION

The new cultivar is a product of a planned breeding program conducted by the inventor to produce *Buddleia davidii* with new flower colors and plant forms with compact habits. The crossing resulting in the new cultivar was made in summer of 2020 at a nursery in Grand Haven, Michigan.

The seed parent is the cultivar *Buddleia davidii* 'SMNBDB', U.S. Plant Pat. No. 33,565. The pollen parent is the cultivar *Buddleia davidii* 'Miss Molly', U.S. Plant Pat. No. 23,425. The new cultivar was found and selected by the inventor in summer of 2022 at the same nursery in Grand Haven, Michigan.

Asexual reproduction of the new cultivar 'SMNBDFRI' was first performed during summer of 2022 in Grand Haven, Michigan, by softwood cuttings. Through subsequent propagation, multiple additional generations have been reproduced, having shown that the unique features of this cultivar are stable and reproduced true to type.

SUMMARY OF THE INVENTION

The cultivar 'SMNBDFRI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNBDFRI'. These characteristics in combination distinguish 'SMNBDFRI' as a new and distinct *Buddleia* cultivar:

1. Dwarf, compact habit.
2. Large, dark green, leathery leaves.
3. Bright, magenta-colored petals.
4. Dense, large inflorescences that are conical in shape with a slight curling aspect.
5. Fragrant flowers.

PARENT COMPARISONS

Plants of 'SMNBDFRI' are similar to plants of the seed parent in most horticultural characteristics, however, plants of 'SMNBDFRI' differ in the following:

1. Flower color of the new cultivar is a darker pink than the flower color of the seed parent.
2. Flower panicles of the new cultivar are more curled than the flower panicles of the seed parent.

Plants of 'SMNBDFRI' are similar to plants of the pollen parent in most horticultural characteristics, however, plants of 'SMNBDFRI' differ in the following:

1. Plants of the new cultivar are a smaller mature size than plants of the pollen parent.
2. Plants of the new cultivar are more compact than plants of the pollen parent.
3. Flower panicles of the new cultivar are larger than flower panicles of the pollen parent.

COMMERCIAL COMPARISON

Plants of 'SMNBDFRI' can be compared to plants of the commercial cultivar *Buddleia davidii* 'BOTEX 006' U.S. Plant Pat. No. 34,500. Plants of 'SMNBDFRI' are similar to plants of 'BOTEX 006' in most horticultural characteristics, however, plants of 'SMNBDFRI' differ in the following:

1. Sepal apex of the new cultivar is acute, while the sepal apex of this comparator is rounded/obtuse.

2. Flower color of the new cultivar is magenta (Red-Purple 72A), while the flower color of this comparator is bright pink (Red-Purple 58B).
3. Flower panicles of the new cultivar have a slightly curling aspect, while the flower panicles of this comparator exhibit little to no curling.

BRIEF DESCRIPTION OF THE PHOTOGRAPHS

The accompanying photograph in FIG. 1 illustrates in full color a typical plant of 'SMNBDFRI' grown outdoors in Grand Haven, Michigan. This plant is approximately 2 years old.

Figure 2:
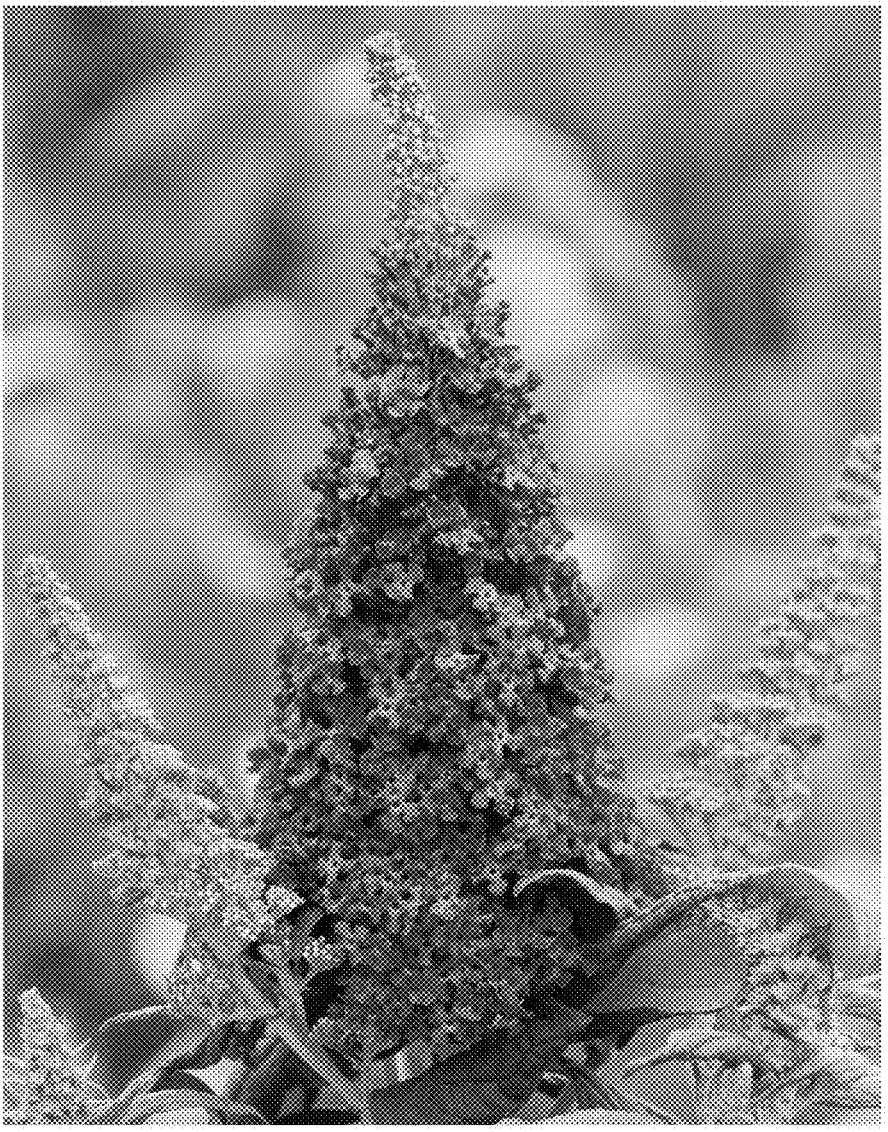

FIG. 2 illustrates in full color a close up of a flower of 'SMNBDFRI'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNBDFRI' plants grown in a poly-greenhouse in Grand Haven, Michigan. The plants were 2 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Buddleia davidii* 'SMNBDFRI'.

PROPAGATION

Typical method: Softwood cuttings.
Root initiation: 14 days in summer at 25° C.
Time to produce rooted cutting: About 40 days in summer at 25° C.
Roots: Dense, freely branching, fine, fibrous. Tan in color, not accurately measured with R.H.S. chart.

PLANT

Plant type: Perennial shrub.
Growth habit: Compact, rounded.
Shape: Globose.
Height: 40 cm.
Plant spread: 40 cm.
Pot size of plant described: 2 gallon.
Age of plant described: 2 to 3 years.
Growth rate: Moderate to high.
Plant vigor: High.
Stem:
- *Branching*.—Basal and lateral.
- *Pinching*.—Some required to encourage well-rounded habit.
- *Number of lateral branches*.—10 to 15.
- *Shape*.—Square.
- *Color*.—Immature: R.H.S. Yellow-Green 148C. Mature: Near R.H.S. Grey-Brown 199C.
- *Length*.—30 cm.
- *Width*.—4 mm.
- *Aspect*.—0° to 30° from vertical.
- *Strength*.—Moderate to high.
- *Texture*.—Pubescent. Medium.
- *Internode length*.—2.75 cm.

FOLIAGE

Leaf:
- *Arrangement*.—Opposite, single.
- *Shape*.—Narrowly elliptic.
- *Length*.—12 cm.
- *Width*.—4 cm.
- *Apex*.—Acuminate.
- *Base*.—Rounded.
- *Margin*.—Serrulate.
- *Texture of top surface*.—Very lightly pubescent; coriaceous.
- *Texture of bottom surface*.—Lightly pubescent, coriaceous with raised venation.
- *Leaf bulging between veins*.—Upper surface: Weak. Lower surface: Medium.
- *Pubescence*.—Yes, both sides.
- *Color*.—Young Foliage, Upper Side: R.H.S. Yellow-Green 147A. Young Foliage, Under Side: R.H.S. Greyed-Green 198B. Mature Foliage, Upper Side: R.H.S. Yellow-Green 147A. Mature Foliage, Under Side: R.H.S. Greyed-Green 198B.

Venation:
- *Type*.—Pinnate. Color: Mature, Upper Side: R.H.S. Yellow-Green 148C. Mature, Under Side: R.H.S. Yellow-Green 148C.

Petiole:
- *Length*.—5 mm.
- *Width*.—2 mm.
- *Color*.—Upper Side: R.H.S. Yellow-Green 148C. Under Side: R.H.S. Yellow-Green 148C.
- *Texture*.—Upper Side: Pubescent. Under Side: Pubescent.

FLOWER

Natural flowering season: Summer.
Flower arrangement: Inflorescence.
Inflorescence type: Panicle.
Height: 13 cm.
Diameter: 6 cm.
Quantity: 1000 to 2000 flowers per inflorescence.
Fragrance: Sweet and floral, moderate intensity.
Flower:
- *Type or form*.—Salverform.
- *Aspect*.—Outward.
- *Length*.—1 cm.
- *Diameter*.—6 mm.
- *Depth*.—6 mm.
- *Persistence*.—Persistent.
- *Longevity*.—About 1 week.

Bud:
- *Length*.—1 cm.
- *Diameter*.—1 mm.
- *Shape*.—Oblong with a flared, square tip.
- *Color*.—R.H.S. Red-Purple 64A, Red-Purple 71A at tip.

Petals:
- *Number*.—4.
- *Arrangement*.—Cruciform. Free.
- *Shape*.—Globose.
- *Tip*.—Obtuse.
- *Base*.—Fused.

*Margin*.—Entire.
*Length*.—2 mm.
*Width*.—3 mm.
*Texture*.—Upper side: Soft and silky. Under side: Soft and silky.
*Color*.—When Opening, Upper Side: R.H.S. Red-Purple 72A. When Opening, Under Side: R.H.S. Red-Purple 72A. Fully Opened, Upper Side: R.H.S. Red-Purple 72A. Irregular blotching with age near throat opening 69C or 69D on some flowers. Fully Opened, Under Side: R.H.S. Red-Purple 72A. Throat Color: R.H.S. Yellow-Orange 15A. Tube Color: R.H.S. Red-Purple 64A.

Sepals:
*Number*.—4.
*Arrangement*.—Whorl; narrowly deltate; fairly inconspicuous.
*Shape*.—Triangular.
*Tip*.—Acute.
*Base*.—Fused.
*Margin*.—Entire.
*Length*.—1 mm.
*Width*.—0.5 mm.
*Texture*.—Upper side: Glabrous. Under side: Glabrous.
*Color*.—Mature, Upper Side: R.H.S. Green 138A. Mature, Under Side: R.H.S. Green 138A.

Calyx:
*Shape*.—Oblong, with narrow, triangular sepals.
*Length*.—2 mm.
*Diameter*.—1 mm.

Peduncle:
*Terminal length*.—15 cm.
*Terminal diameter*.—5 mm.
*Angle*.—0° from vertical.
*Strength*.—High.
*Texture*.—Moderately pubescent.
*Color*.—R.H.S. Yellow-Green 144A.

Pedicel:
*Length*.—1 cm.
*Diameter*.—1 mm.
*Angle*.—45° from vertical.
*Strength*.—Moderate.
*Texture*.—Moderately pubescent.
*Color*.—R.H.S. Yellow-Green 144A.

REPRODUCTIVE ORGANS

Stamens:
*Number*.—2.
*Filament length*.—No filament, anthers fused directly to interior of throat.

Anthers:
*Shape*.—Linear.
*Length*.—1 mm.
*Color*.—R.H.S. Yellow 4D.
*Pollen amount*.—Moderate.
*Pollen color*.—R.H.S. Yellow 4D.

Pistil:
*Number*.—1.
*Length*.—1 mm.

Stigma:
*Shape*.—Linear.
*Color*.—R.H.S. Yellow-Green 144B.
*Style length*.—0.5 mm.
*Style color*.—R.H.S. Yellow-Green 144B.
*Ovary color*.—R.H.S. Yellow-Green 144B.

OTHER CHARACTERISTICS

Fruit and seed: Not observed to date.
Disease resistance: Resistance and susceptibility to typical diseases and pests of *Buddleia* not observed to date.
Drought tolerance and cold tolerance: Hardy to USDA Zones 5 to 9.

What is claimed is:

1. A new and distinct cultivar of *Buddleia* plant named 'SMNBDFRI' as herein illustrated and described.

* * * * *